(12) United States Patent
Ales et al.

(10) Patent No.: US 8,101,813 B2
(45) Date of Patent: Jan. 24, 2012

(54) TRAINING PROGRESS INDICATOR

(75) Inventors: Thomas Michael Ales, Neenah, WI (US); Keith William Magic, Clarkston, MI (US); Shawn Jeffery Sullivan, Neenah, WI (US); Davis-Dang H. Nhan, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 543 days.

(21) Appl. No.: 12/261,658

(22) Filed: Oct. 30, 2008

(65) Prior Publication Data

US 2010/0114046 A1   May 6, 2010

(51) Int. Cl.
*A61F 13/15*   (2006.01)

(52) U.S. Cl. .................. 604/361; 604/359; 604/360

(58) Field of Classification Search .............. 604/361, 604/359, 360
See application file for complete search history.

(56) References Cited

U.S. PATENT DOCUMENTS

| | | |
|---|---|---|
| 3,675,654 A | 7/1972 | Baker et al. |
| 3,731,685 A | 5/1973 | Eidus |
| 4,022,211 A | 5/1977 | Timmons et al. |
| 4,100,324 A | 7/1978 | Anderson et al. |
| 4,192,311 A | 3/1980 | Felfoldi |
| 4,292,916 A | 10/1981 | Bradley et al. |
| 4,327,731 A | 5/1982 | Powell |
| 4,366,241 A | 12/1982 | Tom et al. |
| 4,734,238 A | 3/1988 | Sugimori et al. |
| 4,812,053 A | 3/1989 | Bhattacharjee |
| 4,903,254 A | 2/1990 | Haas |
| 4,931,051 A | 6/1990 | Castello |
| 4,940,464 A | 7/1990 | Van Gompel et al. |
| 4,987,849 A | 1/1991 | Sherman |
| 5,006,711 A | 4/1991 | Hamashima et al. |
| 5,045,283 A | 9/1991 | Patel |
| 5,053,339 A | 10/1991 | Patel |
| 5,058,088 A | 10/1991 | Haas et al. |
| 5,089,548 A | 2/1992 | Zimmel et al. |
| 5,284,703 A | 2/1994 | Everhart et al. |
| 5,350,625 A | 9/1994 | Peterson et al. |
| 5,352,582 A | 10/1994 | Lichtenwalter et al. |
| 5,389,093 A | 2/1995 | Howell |
| 5,486,166 A | 1/1996 | Bishop et al. |

(Continued)

FOREIGN PATENT DOCUMENTS

DE   10 2007 006 230 A1   8/2008

(Continued)

OTHER PUBLICATIONS

International Search Report and Written Opinion, PCT/IB2009/053870, mailed Aug. 23, 2010.

*Primary Examiner* — Jacqueline F Stephens
(74) *Attorney, Agent, or Firm* — Dority & Manning, P.A.

(57) ABSTRACT

The present subject matter relates to absorbent articles and signaling devices for use therewith. An absorbent article may be provided with selected electrical components used as wetness or other type sensors which may be determined by a coupled signaling device. An attached signaling device may automatically determine physiological changes of a wearer of the absorbent article including increases in void volume over time, increases in time between voids and proximity to bathroom fixtures. The signaling device may provide data analysis and/or display, and may provide remote alarm functions.

18 Claims, 4 Drawing Sheets

U.S. PATENT DOCUMENTS

| | | |
|---|---|---|
| 5,490,846 A | 2/1996 | Ellis et al. |
| 5,602,804 A | 2/1997 | Haas |
| 5,645,542 A | 7/1997 | Anjur et al. |
| 5,681,298 A | 10/1997 | Brunner et al. |
| 5,719,828 A | 2/1998 | Haas et al. |
| 5,726,435 A | 3/1998 | Hara et al. |
| 5,766,389 A | 6/1998 | Brandon et al. |
| 5,785,354 A | 7/1998 | Haas |
| 5,820,973 A | 10/1998 | Dodge, II et al. |
| 5,854,148 A | 12/1998 | Asada et al. |
| 5,954,512 A | 9/1999 | Fruge |
| 5,989,923 A | 11/1999 | Lowe et al. |
| 6,200,250 B1 | 3/2001 | Janszen |
| 6,200,765 B1 | 3/2001 | Murphy et al. |
| 6,250,929 B1 | 6/2001 | Kolb et al. |
| 6,294,392 B1 | 9/2001 | Kuhr et al. |
| 6,295,252 B1 | 9/2001 | Holt et al. |
| 6,297,424 B1 | 10/2001 | Olson et al. |
| 6,307,119 B1 | 10/2001 | Cammarota et al. |
| 6,362,389 B1 | 3/2002 | McDowall et al. |
| 6,417,455 B1 | 7/2002 | Zein et al. |
| 6,436,651 B1 | 8/2002 | Everhart et al. |
| 6,610,386 B2 | 8/2003 | Williams et al. |
| 6,642,427 B2 | 11/2003 | Roe et al. |
| 6,645,190 B1 | 11/2003 | Olson et al. |
| 6,710,221 B1 | 3/2004 | Pierce et al. |
| 6,713,660 B1 | 3/2004 | Roe et al. |
| 6,722,886 B2 | 4/2004 | Blumberg |
| 6,752,430 B2 | 6/2004 | Holt et al. |
| 6,772,708 B2 | 8/2004 | Klofta et al. |
| 6,786,412 B2 | 9/2004 | Shimizu |
| 6,856,249 B2 | 2/2005 | Strubbe et al. |
| 6,904,865 B2 | 6/2005 | Klofta et al. |
| 6,997,384 B2 | 2/2006 | Hara |
| 7,195,165 B2 | 3/2007 | Kesler et al. |
| 7,306,764 B2 | 12/2007 | Mody |
| 7,321,315 B2 | 1/2008 | Brumm et al. |
| 7,332,642 B2 | 2/2008 | Liu |
| 7,355,090 B2 * | 4/2008 | Ales et al. ............ 604/361 |
| 7,674,747 B1 | 3/2010 | Long |
| 7,722,357 B2 | 5/2010 | Payette-Hebert et al. |
| 2001/0031954 A1 | 10/2001 | Jordan et al. |
| 2004/0055367 A1 | 3/2004 | Swiecicki et al. |
| 2004/0078219 A1 | 4/2004 | Kaylor et al. |
| 2005/0065489 A1 | 3/2005 | Driskell et al. |
| 2005/0101841 A9 | 5/2005 | Kaylor et al. |
| 2005/0112085 A1 | 5/2005 | MacDonald et al. |
| 2005/0137543 A1 | 6/2005 | Underhill et al. |
| 2005/0217791 A1 | 10/2005 | Costello et al. |
| 2005/0252967 A1 | 11/2005 | Kesler et al. |
| 2006/0114754 A1 | 6/2006 | MacDonald et al. |
| 2006/0149197 A1 | 7/2006 | Niemeyer |
| 2006/0224443 A1 | 10/2006 | Soza et al. |
| 2006/0229577 A1 | 10/2006 | Roe et al. |
| 2007/0071320 A1 | 3/2007 | Yada |
| 2007/0079748 A1 | 4/2007 | Ahmed et al. |
| 2007/0138286 A1 | 6/2007 | Kamijoh et al. |
| 2007/0149936 A1 | 6/2007 | Weber et al. |
| 2007/0199994 A1 | 8/2007 | Cattrone et al. |
| 2007/0259997 A1 | 11/2007 | Bakker et al. |
| 2007/0282286 A1 | 12/2007 | Collins et al. |
| 2008/0147031 A1 | 6/2008 | Long et al. |
| 2008/0243099 A1 | 10/2008 | Tippey et al. |
| 2009/0050700 A1 | 2/2009 | Kamijoh et al. |
| 2009/0062757 A1 | 3/2009 | Long et al. |
| 2009/0155753 A1 | 6/2009 | Ales et al. |
| 2009/0247979 A1 | 10/2009 | Sosalla et al. |
| 2009/0326491 A1 | 12/2009 | Long et al. |
| 2010/0164733 A1 | 7/2010 | Ales et al. |
| 2010/0168694 A1 | 7/2010 | Gakhar et al. |
| 2011/0015063 A1 | 1/2011 | Gil et al. |
| 2011/0015597 A1 | 1/2011 | Gil et al. |

FOREIGN PATENT DOCUMENTS

| | | |
|---|---|---|
| EP | 1 398 014 A2 | 3/2004 |
| JP | 4143876 A | 5/1992 |
| JP | 2002022688 | 1/2002 |
| JP | 2003 058759 A | 2/2003 |
| JP | 2004529730 | 9/2004 |
| JP | 2005-000602 | 1/2005 |
| JP | 2006-043389 | 2/2006 |
| JP | 2006-068466 | 3/2006 |
| JP | 2006 249638 A | 9/2006 |
| JP | 2007-007352 | 1/2007 |
| JP | 2007-286024 | 11/2007 |
| JP | 2009 280946 A | 12/2009 |
| WO | WO 96/08788 A1 | 3/1996 |
| WO | WO 00/37009 | 6/2000 |
| WO | WO 00/65348 A2 | 11/2000 |
| WO | WO 2004/084765 A2 | 10/2004 |
| WO | WO 2008/072116 A1 | 6/2008 |
| WO | WO 2010/015881 A1 | 2/2010 |

* cited by examiner

FIG. 2
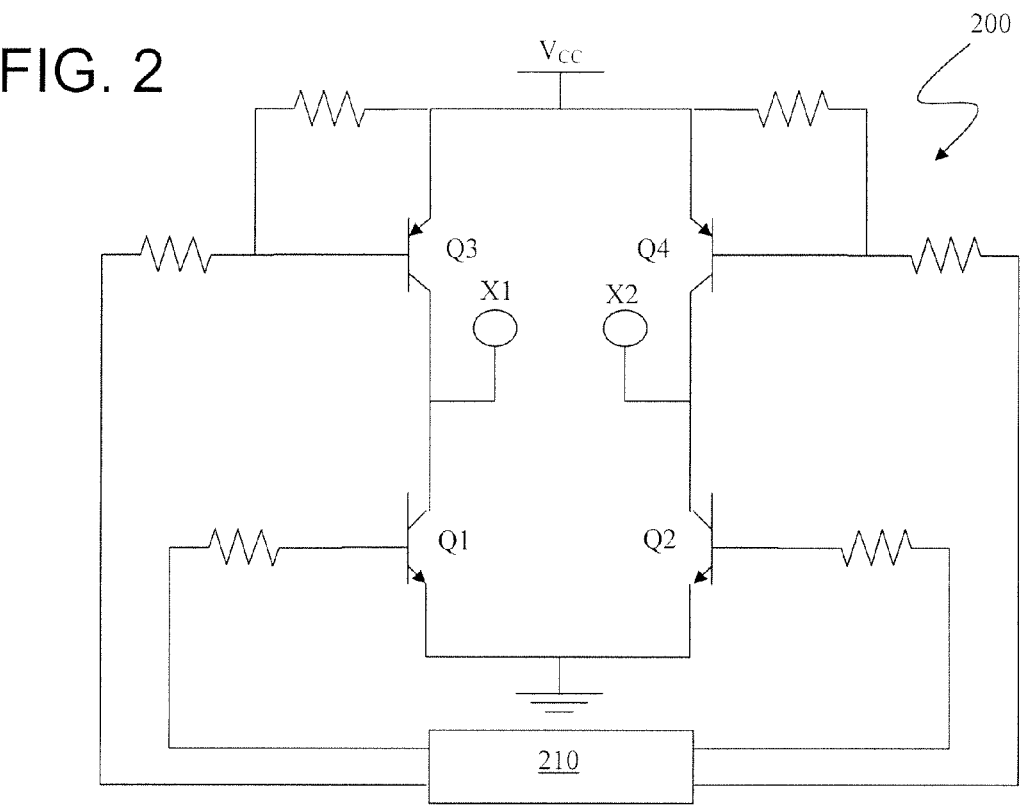
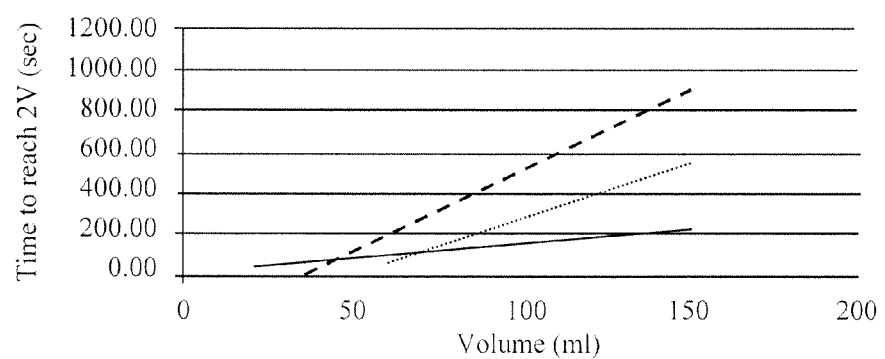
FIG. 3

TRAINING PROGRESS INDICATOR

BACKGROUND OF THE INVENTION

Absorbent articles such as diapers, training pants, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices produce either a visual or an audible signal.

In some previously known arrangements, for instance, inexpensive conductive threads, foils, or paper have been placed in the absorbent articles in the machine direction. The conductive materials serve as conductive leads for a signaling device and form an open circuit in the article that can be closed when a body fluid, such as urine, closes the circuit. In these arrangements, although the absorbent articles may be disposable, the signaling devices are not. Thus, the signaling devices are intended to be removed from the article and reattached to a subsequent article.

Problems, however, have been encountered in employing such products with respect to potty training children in that the signals produced by such products generally relate only to the detection of wetness. It would be beneficial if alternative signaling in the form of positive feedback were available to encourage children or their trainers to take or encourage actions that will assist the child in developing health and hygiene life skills. Similarly, problems have been encountered in employing such products with respect to adult care systems. It would, likewise be beneficial if signaling in the form of information relayed to a caregiver and/or wearer provided information regarding changes in void size and/or spacing that could be indicative of health concerns.

SUMMARY OF THE INVENTION

In general, the present disclosure is directed to improved sensing and signaling arrangements and methodologies for use with a variety of absorbent articles for providing indications to a parent or guardian that potty training progress has been made. Additionally, such signaling arrangements and methodologies may be employed in adult care setting involving adult life skills assessment and/or training addressing such as, but not limited to, enuresis (bedwetting). Signaling devices corresponding to various configurations may be attached in whole or in part by appropriate mechanisms to disposable absorbent articles. The signaling device, for instance, may be configured as a single device attached to an absorbent article or may correspond to separate components with one component attached to the absorbent article and one component remote from the absorbent article and may as a single device or collectively be configured to indicate to a user increases in amounts of body fluid volume and/or increase in time between detection of fluids. For example, in one embodiment, the absorbent article comprises a diaper and the signaling device is configured to indicate the presence of urine or of a bowel movement. In other embodiments, however, the signaling device may be configured to indicate the physical location of a diaper wearer relative to a bathroom fixture. In all embodiments, the signaling device may provide feedback to the parent, guardian, and/or wearer to encourage appropriate action to be taken for health and hygiene life skills training.

In one embodiment, a system is provided comprising a chassis configured to be worn by an individual. The chassis comprises an outer cover having an interior surface and an exterior surface and an absorbent structure positioned adjacent the interior surface of the outer cover. At least one conductive element is contained in the chassis and forms part of a sensing circuit that is configured to sense physiological changes of a wearer. At least one electrical device is associated with the at least one conductive element, which electrical device is configured to indicate sensed physiological changes related to the wearer. As used herein, physiological changes are meant to include both changes in a wearer resulting in an insult to an absorbent article as well as changes in the physical location of a wearer.

In particular embodiments the at least one electrical device is directly coupled to the at least one conductive element although in other embodiments wireless coupling to a remote component of the electrical device may be used. In certain embodiments the at least one conductive element comprises at least one pair of conductive elements and the at least one electrical device comprises an indicator configured to indicate one of increases in void volume of a wearer over time and increases in time between voids of a wearer.

In still further embodiments a system is provided wherein the at least one electrical device comprises an indicator configured to indicated proximity of a wearer to one of a predetermined item and a predetermined location. In particular embodiments, proximity of a wearer to a fixture in a bathroom may be indicated.

In yet still further embodiments a system is provide to provide a signal at a location remote from the chassis and wearer that signals sensed physiological changes to alert a parent or guardian of the changes.

In accordance with still further embodiments a memory may be provided and configured to store data representing sensed physiological changes. In particular embodiments data may be transferred from the memory to a computer or other device to provide indicia representative of the data. Data may be transferred by any suitable means including by one of direct electrical connection, USB connection, wireless connection, Bluetooth connection, WiFi connection, and optical connection.

In yet still further embodiments a visual display of data trend tracking over time as well as audible and visual alarms based on data received from the electrical device may be provided either locally or at a remote location.

Other embodiments of the present subject matter also relate to methodologies for providing physiological change related signals comprising providing a wearable absorbent article that includes an absorbent structure and at least one conductive element that forms part of a sensing circuit configured to sense physiological changes of a wearer. A signaling device is provide that is capable of producing humanly perceptible signals responsive to sensed physiological changes of a wearer the signaling device is coupled to the absorbent article. In particular methods, the signaling device may be directly connected or wirelessly coupled to the absorbent article.

In accordance with further methodologies, the signaling device may be responsive to one or more of increases in void volume over time of a wearer, increases in the time between voids of the wearer, and proximity of the wearer to a bathroom fixture. Alternative methodologies provide for voice instructions to be delivered to a wearer of the absorbent article.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIG. 2 is a schematic diagram of an exemplary pulse circuit usable in conjunction with components of the absorbent article to detect and/or measure insults to the absorbent article;

FIG. 3 is a graph depicting a rate of change of voltage vs. volume insulted to the absorbent article;

Figure 1:
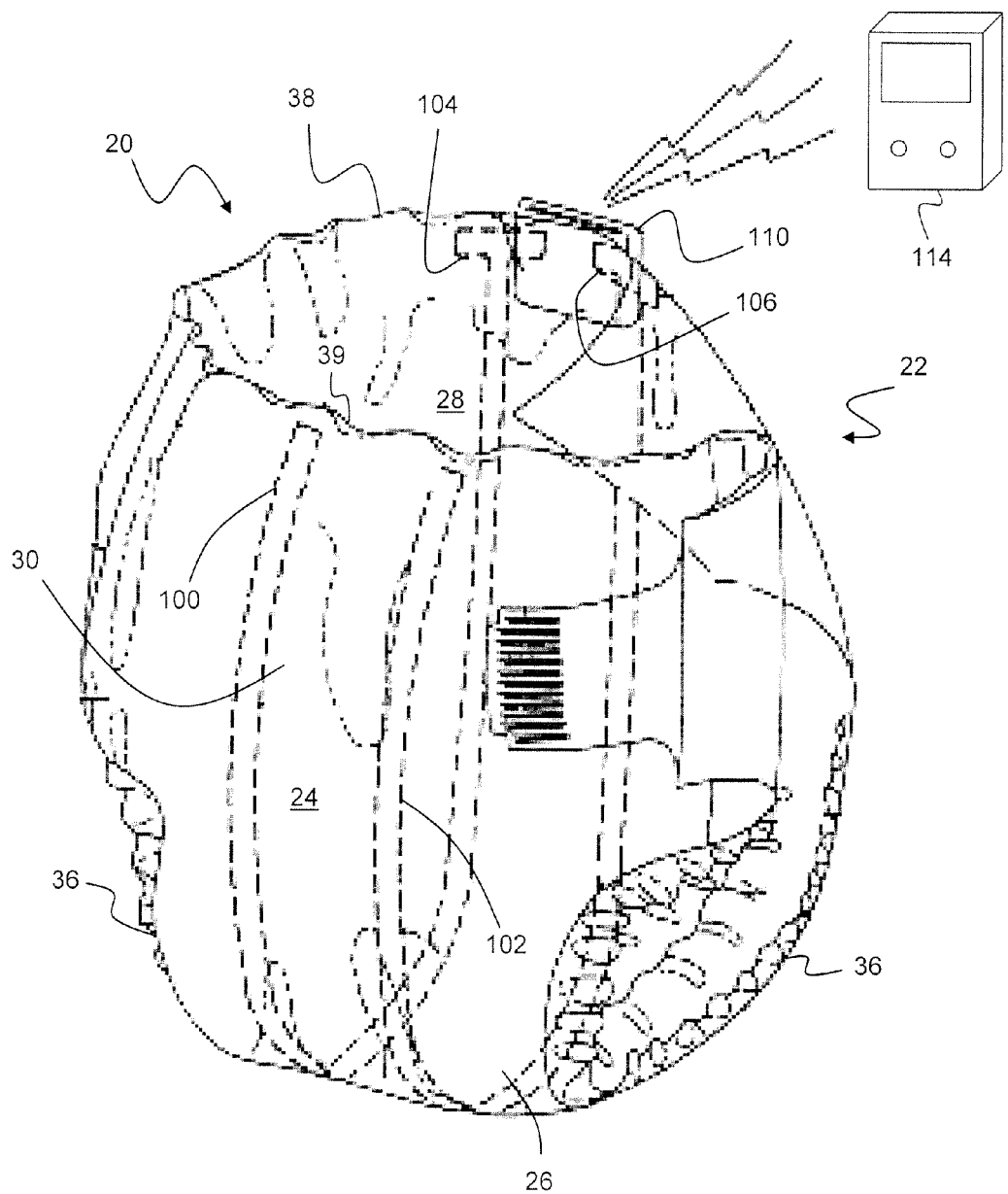
FIG. 1 is a rear perspective view of one embodiment of an absorbent article made in accordance with the present invention.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to absorbent articles adapted to be attached to a signaling device that may be configured to indicate the presence of a body fluid in the absorbent article or other changes in the condition of the product or wearer. The absorbent article may be, for instance, a diaper or a training pant, and the like. It should be appreciated that while the present disclosure is more generally described with respect to articles designed to be worn by children, such is not a limitation of the present subject matter. In fact, absorbent articles designed for use in adult care setting may equally benefit from present disclosure. Absorbent articles made according to the present disclosure may include a sensing circuit that detects when a conductive fluid, such as a body fluid, is sensed between a pair of conductive leads. Generally, the absorbent articles containing the sensing circuit are disposable meaning that they are designed to be discarded after a limited use rather than being laundered or otherwise restored for reuse.

A sensing circuit contained within the absorbent articles in accordance with the present subject matter is configured to be attached to a signaling device. The signaling device can provide power to the sensing circuit while also optionally including some type of audible and/or visible signal that indicates to the user the presence of, or characteristics related to, a body fluid. In alternate embodiments, the signaling device may correspond to multiple portions with a portion attached to the absorbent article and another portion space from and wirelessly coupled to the portion attached to the absorbent article. Although the absorbent article itself is disposable, the signaling device may be reusable from article to article. In this regard, the present disclosure is particularly directed to determining selected physiological changes related to the absorbent article.

This present subject matter describes instrumentation and signal analysis that can measure the volume and concentration of an insult in an absorbable disposable garment as well as numbers of insults over time and time periods between insults. The system herein disclosed may correspond to two individual components: an absorbent disposable pant with conductive foils placed beneath the liner, and a semi-durable sensor which incorporates a pulse circuit and a DC power supply. The absorbent pant may correspond to a training pant with parallel conductive foils placed beneath the liner of the pant. In an exemplary configuration, the present subject matter may be incorporated within and used with HUGGIES™ Pull-Ups® training pant.

Referring to FIG. 1, for exemplary purposes, an absorbent article 20 that may be made in accordance with the present subject matter is shown. The absorbent article 20 may or may not be disposable. It should be understood that the present subject matter is suitable for use with various other absorbent articles intended for personal wear, including but not limited to diapers and training pants, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Diaper 20 is representatively illustrated in FIG. 1 in a partially fastened condition and defines a pair of longitudinal end regions, otherwise referred to herein as a front region 22 and a back region 24, and a center region, otherwise referred to herein as a crotch region 26, extending longitudinally between and interconnecting the front and back regions 22, 24. Diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

A signaling device 110 is shown attached to conductive pad members 104 and 106. Signaling device 110 includes a pair of opposing terminals that are electrically connected to the corresponding conductive pad members. When a body fluid is present in the absorbent article 20, the open circuit formed by the conductive elements 100 and 102 together with circuitry within signaling device 110 senses the fluid and, in turn, activates additional circuitry within signaling device 110 to record aspects of the sensed fluid for purposes as will be more fully described later.

Signaling device 110 can emit an audible and/or visual signal and/or can transmit information to a remote portion 114 of the sensor system. Remote portion 114 may correspond to a dedicated device or may correspond to, such as, a personal computer, which may be used to analyze and/or display information from signaling device 110. In an alternative configuration data received by remote portion 114 may be transferred to a personal computer by any suitable means for storage, display, and/or further analysis. In exemplary configurations, data may be transferred from signaling device 110 to remote portion 114 and from remote portion 114 to a personal computer (not illustrated) and/or directly to a personal computer from remote portion 114 by a variety of well known ways including, but not limited to, direct coupling via a cable, optical coupling, and/or wireless coupling. Wireless communications may be conducted over such as Bluetooth, WiFi, or other like arrangements.

With reference now to FIG. 2, there is schematically illustrated a pulse circuit 200 which is designed to take a reading with signal processing circuit 220 as controller 210 causes transistors Q1-Q4 to alternately excite and ground conductive foils 100, 102 to emulate AC excitation of the foils using DC source $V_{CC}$. Conductive foils 100, 102 may be connected to terminals X1, X2, respectively by appropriate electrical connectors. In addition, pulse circuit 200 is configured to decrease the time the strips are excited in order to reduce the ionization of particles, therefore prolonging the conductive life of the foils. In an exemplary configuration the power supply ($V_{CC}$) may correspond to a DC 3 volt battery.

In operation, signal processing circuit 220 measures both the volume and the concentration (specific gravity) of urine from an insult in an absorbable disposable garment during use. This will be accomplished by measuring several electrical properties of the system. A dry product, with power supplied, will exhibit an infinite resistance because there is no connection between the foils. When an ionic solution (such as urine) is introduced to the product, an electrical path between the two conductive foils 100, 102 is created. While completing the circuit, the ionic solution introduces a variable impedance to the system. The impedance produced by the conductive ionic solution varies depending on the adsorption of the solution by the product. Smaller volumes will absorb faster than larger volumes, and therefore the rate of change of impedance with smaller volumes will be different than that of larger volumes. Since the voltage of a system is directly proportional to the impedance, the volume of urine insulted is determined by measuring the rate of change in voltage across conductive foils 100, 102. FIG. 3 illustrates the rate of change in voltage compared to the volume insulted for several exemplary samples.

Figure 4A:
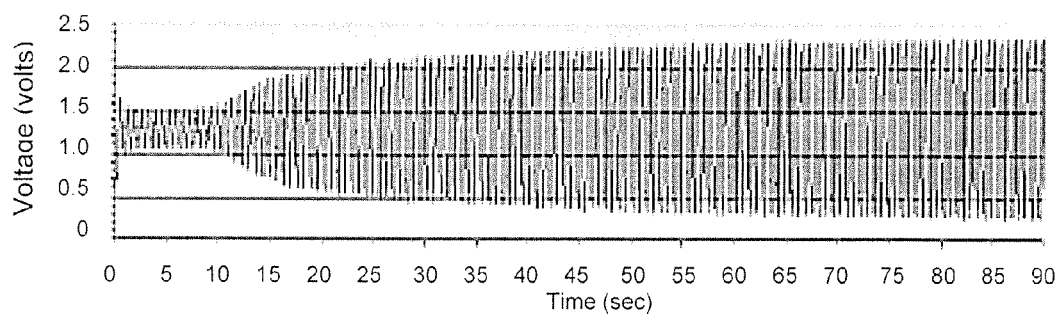
FIGS. 4A, 4B, and 4C illustrate various rates of voltage return over time depending on ionic concentration of the insult.
Figure 4B:
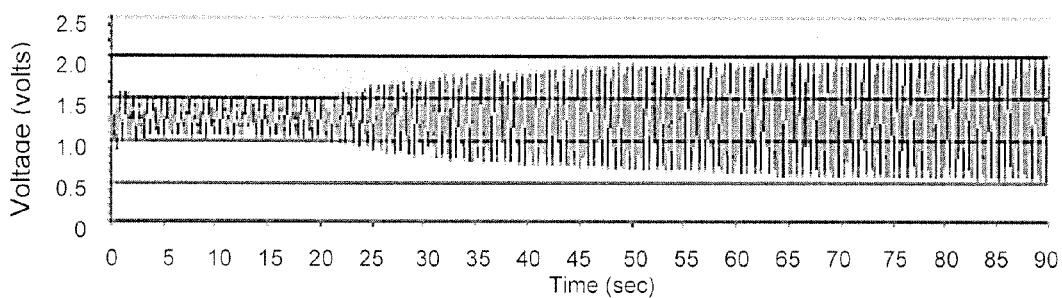
Figure 4C:
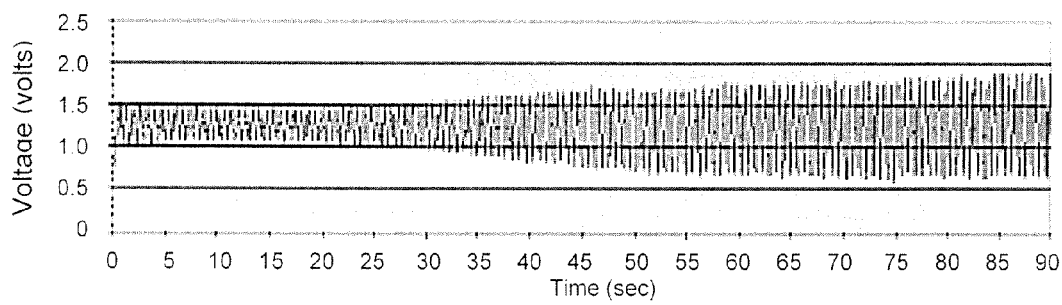

Along with the previously mentioned attributes that pulse circuit 200 provides, the emulated AC excitation of the circuit also induces a capacitive charge/discharge with ionic solution, much like that of a capacitor. There are several different ways to determine the concentration of an insult by investigating this capacitive property. The first method simply looks at the envelope of the oscillation of the voltage output over a period of time after an insult. The rate of voltage return measured by circuit 220 during this time period is different for each ionic concentration of solution used. FIGS. 4A, 4B, and 4C illustrate the voltage output oscillations for three different concentrations of solutions used over a 90 second time period. The exemplary results illustrated in FIGS. 4A, 4B, and 4C were obtained using 60 ml each of solutions with specific gravities of 1.001. 1.02. and 1.037, respectively. By comparing the rate of voltage return, the concentration of solution can be determined.

Figure 5A:
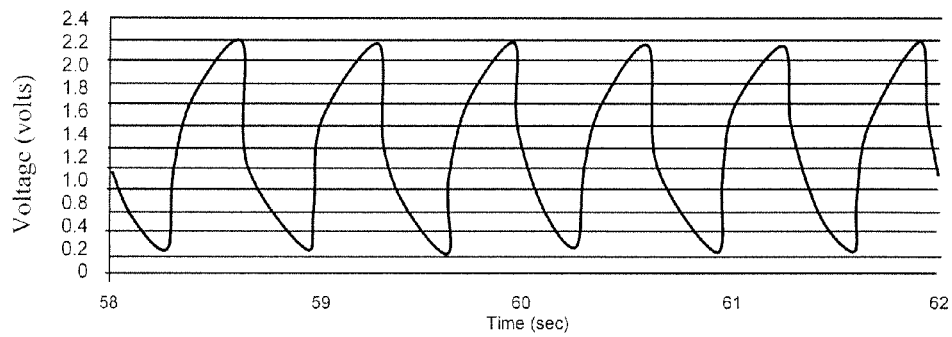
FIGS. 5A, 5B, and 5C illustrate various waveform slopes that may be used in an alternative method to determine ionic concentration.
Figure 5B:
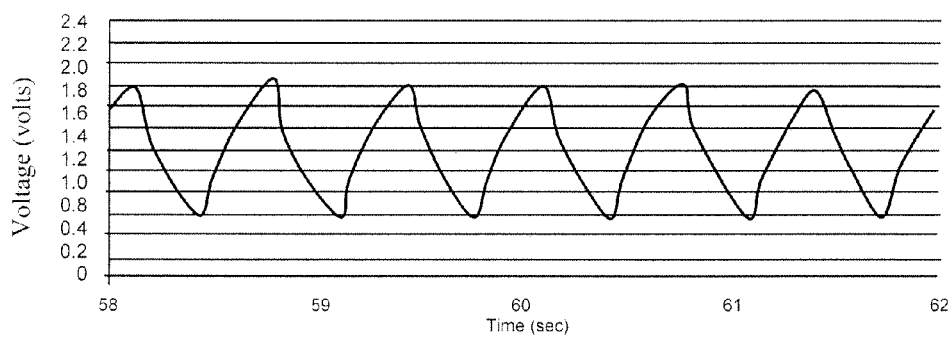
Figure 5C:
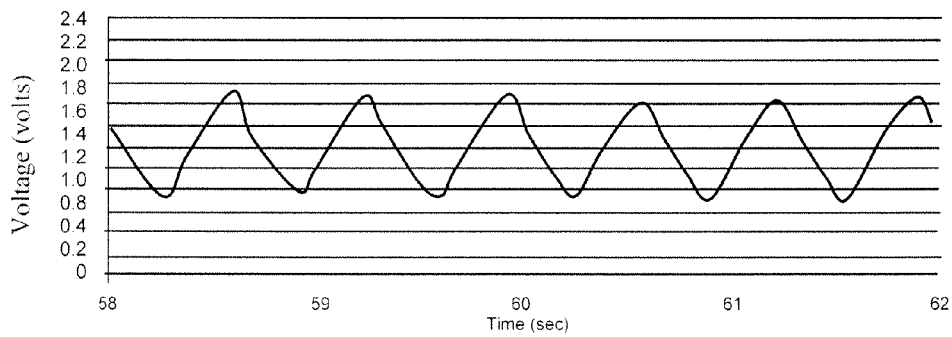

Other methods for determining insult concentrations may examine the shape of the charge/discharge waveform produced. The shape of this voltage charge/discharge waveform for an insult changes over time. A dry product will produce a square wave function representing the pulse. After an insult occurs the waveform flattens to a linear oscillation and changes to a sawtooth wave, becoming more pronounced over time until it eventually returns to the original square wave. At a given time point, each ionic concentration of urine will display waveforms distinctly different from each other. This trend can be measured and used to determine the ionic concentration of an insult in several ways. FIGS. 5A, 5B, and 5C illustrate exemplary charge/discharge waveforms at 60 seconds after an insult for three solutions of different ionic concentrations corresponding to the same volume and specific gravities as employed in the respective FIGS. 4A, 4B, and 4C. From the figures it can be seen how at the same time point, each solution displays a different shaped waveform. The areas under the curves from each solution are independent of those from the others and can be measured to determine the ionic concentration they represent.

In an alternative method for determining ionic concentration, the slope of the waveforms at a given time point may be examined. The slope of the curves for each solution in FIGS. 5A, 5B, and 5C are unique to their specific concentration. The slope of the waveform at a given time point could therefore be used to differentiate between different ion concentrations of urine. Testing of several products under these electrical conditions showed consistent and repeatable data for the correlation of volume and concentration of an insult in the product. Through repetitive testing, a calibration curve can be established for each analysis. Such a calibration curve could then be used in a device to monitor electrical conditions of the product. Measurement and signal analysis may be performed by an on board processor and/or by associated additional sensor and display devices including, but not limited to, personal computers (PC).

A system constructed in accordance with present disclosure may correspond to a semi-durable sensor that can be clipped onto the back of a pant product with conductive foils beneath the liner. The sensor will measure the volume and ionic concentration of insult urine as well as the volumes and concentrations of second, third, etc. insults. In an exemplary configuration the sensor 110 (FIG. 1) may contain a visual display screen that will display insult volume, insult concentration, insult time, number of insults, fullness of product, etc. Alternatively, sensor 110 may also transmit data to a separate device 114 (FIG. 1) for display, analysis, and/or storage. Sensor 110 may also communicate with a PC and save all insult information in, for example, a spreadsheet document for later analysis by the parents and/or doctor.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the invention so further described in such appended claims.

What is claimed is:
1. A system, comprising:
   a chassis configured to be worn by an individual comprising an outer cover having an interior surface and an exterior surface and an absorbent structure positioned adjacent the interior surface of the outer cover;

a pair of conductive elements contained in the chassis and forming part of a sensing circuit that is configured to sense physiological changes of a wearer; and at least one electrical device associated with said pair of conductive elements, said at least one electrical device configured to determine and to indicate sensed physiological changes of a wearer comprising at least one of increases in void volume over time, increases in time between voids, and proximity of a wearer to a fixture in a bathroom.

2. A system as defined in claim 1, wherein said at least one electrical device is directly coupled to said pair of conductive elements.

3. A system as defined in claim 1, wherein said at least one electrical device is wirelessly coupled to said pair of conductive elements.

4. A system as defined in claim 1, wherein said at least one electrical device is configured to provide a signal at a location remote from said chassis, said signal indicative of said sensed physiological changes.

5. A system as defined in claim 1, wherein said electrical device further comprises a memory configured to store data representing said sensed physiological changes.

6. A system as defined in claim 5, further comprising:

at least one second electrical device, said at least one second electrical device configured to provide indicia representative of data transferred from said memory of said electrical device.

7. A system as defined in claim 6, wherein said at least one second electrical device comprises a computer.

8. A system as defined in claim 6, wherein said at least one second electrical device is configured to receive data from said electrical device by one of direct electrical connection, USB connection, wireless connection, Bluetooth connection, WiFi connection, and optical connection.

9. A system as defined in claim 6, wherein said at least one second electrical device is configured to provide a visual display of data trend tracking over time.

10. A system as defined in claim 6, wherein said at least one second electrical device is configured to provide at least one of audible and visual alarms based on data received from said electrical device.

11. A method for providing physiological change related signals, comprising:

providing a wearable absorbent article comprising an absorbent structure and a pair of conductive elements, the pair of conductive elements forming part of a sensing circuit configured to sense physiological changes of a wearer;

providing a signaling device capable of producing humanly perceptible signals;

configuring the signaling device to determine in response to sensed physiological changes of a wearer including at least one of increases in void volume over time, increases in the time between voids, and proximity to a bathroom fixture; and coupling the signaling device to the absorbent article.

12. The method of claim 11, wherein coupling comprises direct coupling.

13. The method of claim 11, wherein coupling comprises wireless coupling.

14. The method of claim 11, further comprising providing voice instructions from the signaling device to a wearer.

15. The method of claim 11, further comprising:

associating a memory with said signaling device;

storing data indicative of one or more of sensed physiological changes of a wearer; and displaying indicia of said stored data.

16. The method of claim 15, further comprising:

transferring stored data from said memory to a remote device; and displaying indicia of the transferred data on the remote device.

17. The method of claim 16, wherein the remote device is a computer.

18. The method of claim 16, wherein transferring stored data comprises transferring data by one of direct electrical connection, USB connection, wireless connection, Bluetooth connection, WiFi connection, and optical connection.

\* \* \* \* \*